(12) United States Patent
Emminger et al.

(10) Patent No.: US 11,976,260 B2
(45) Date of Patent: May 7, 2024

(54) PHOTOBIOREACTOR AND METHOD FOR THE CULTIVATING OF MICROALGAE

(71) Applicant: Beco Invest B.V., Houten (NL)

(72) Inventors: Franz Emminger, Hainburg (AT); Silvia Fluch, Weiden/See (AT)

(73) Assignee: ECODUNA AG, Bruck an der Leitha (AT)

( * ) Notice: Subject to any disclaimer, the term of this patent is extended or adjusted under 35 U.S.C. 154(b) by 542 days.

(21) Appl. No.: 16/329,045

(22) PCT Filed: Aug. 30, 2017

(86) PCT No.: PCT/EP2017/071707
§ 371 (c)(1),
(2) Date: Feb. 27, 2019

(87) PCT Pub. No.: WO2018/041863
PCT Pub. Date: Mar. 8, 2018

(65) Prior Publication Data
US 2019/0218490 A1     Jul. 18, 2019

(30) Foreign Application Priority Data
Aug. 30, 2016  (EP) .................................... 16186440

(51) Int. Cl.
*C12M 1/00* (2006.01)
*C12M 1/12* (2006.01)
*C12N 1/12* (2006.01)

(52) U.S. Cl.
CPC ............ *C12M 21/02* (2013.01); *C12M 23/06* (2013.01); *C12M 23/34* (2013.01); *C12M 29/06* (2013.01); *C12M 39/00* (2013.01); *C12N 1/12* (2013.01)

(58) Field of Classification Search
CPC ........ C12M 1/00; C12M 21/02; C12M 23/06; C12M 23/34; C12M 29/06; C12M 39/00; C12N 1/12
(Continued)

(56) References Cited

U.S. PATENT DOCUMENTS

| 5,001,066 A * | 3/1991 | Hitzman ..................... B01J 8/22 |
| | | 261/127 |
| 2010/0055765 A1* | 3/2010 | Frank ..................... C12M 31/10 |
| | | 435/257.1 |

(Continued)

FOREIGN PATENT DOCUMENTS

| CN | 202968549 U | 6/2013 |
| DE | 10 2009 029 792 | 12/2010 |

(Continued)

OTHER PUBLICATIONS

Int'l Search Report (Form PCT/ISA/210) conducted in Int'l Appln. No. PCT/EP2017/071707 (dated Nov. 28, 2017).

(Continued)

*Primary Examiner* — Liban M Hassan
(74) *Attorney, Agent, or Firm* — Maier & Maier, PLLC

(57) ABSTRACT

The invention relates to a photobioreactor (1) for cultivating phototrophic microorganisms (such as microalgae for example), comprising a reactor element (2) which has a plurality of rising pipes (3a) and falling pipes (3b) for a liquid culture medium (4) containing the microorganisms and which has a distributing pipe (5). The upper ends (6) of each of the rising pipes (3a) and the falling pipes (3b) are connected to the distributing pipe (5) in a liquid-permeable manner. The invention is characterized in that both the culture medium (4) as well as a gas chamber (9) above the culture medium (4) for receiving gas bubbles (10) rising out of the culture medium (4) are provided in the distributing pipe (5) in the operating state, wherein a boundary surface (Continued)

(11) is arranged between the culture medium (4) and the gas chamber (9) in the distributing pipe (5). By arranging the boundary surface (9) (or the boundary surface region), which is typically susceptible to dirt, in the distributing pipe (5), the aim of the invention to simplify the cleaning process of the photobioreactor or the process of keeping same clean is achieved. In this manner, the yield and service life of the photobioreactor is increased. The invention additionally relates to a method for cultivating phototrophic microorganisms.

12 Claims, 5 Drawing Sheets

(58) Field of Classification Search
USPC .................................................. 435/292.1
See application file for complete search history.

(56) References Cited

U.S. PATENT DOCUMENTS

| | | | | |
|---|---|---|---|---|
| 2010/0330652 | A1* | 12/2010 | Mohr | C12M 21/02 435/243 |
| 2011/0027875 | A1* | 2/2011 | Cathcart | C12M 23/44 435/292.1 |
| 2012/0021498 | A1* | 1/2012 | Muller-Feuga | C12M 39/00 435/257.1 |
| 2014/0242681 | A1 | 8/2014 | Fiorentino | |
| 2017/0130181 | A1* | 5/2017 | Emminger | C12M 41/44 |
| 2019/0218491 | A1* | 7/2019 | Emminger | C12M 29/06 |

FOREIGN PATENT DOCUMENTS

| | | | |
|---|---|---|---|
| EP | 1632562 A2 | 3/2006 | |
| EP | 2947139 A1 | 11/2015 | |
| WO | 9409112 A1 | 4/1994 | |
| WO | 2009/051478 | 4/2009 | |
| WO | WO-2009051478 A2 * | 4/2009 | C12M 23/06 |
| WO | WO-2009094680 A1 * | 8/2009 | C12M 23/50 |
| WO | 2010/025345 A2 | 3/2010 | |
| WO | 2011/015653 | 2/2011 | |
| WO | 2014/133793 A1 | 9/2014 | |
| WO | WO-2015102529 A1 * | 7/2015 | C12M 39/00 |
| WO | 2015/179888 | 12/2015 | |
| WO | 2016168871 A2 | 10/2016 | |

OTHER PUBLICATIONS

Int'l Written Opinion (Form PCT/ISA/237) conducted in Int'l Appln. No. PCT/EP2017/071707 (dated Nov. 28, 2017).
Europe Search Report and Office Action conducted in counterpart Europe Appln. No. 16186440.0 (dated Feb. 20, 2017) (w/machine translation).

* cited by examiner

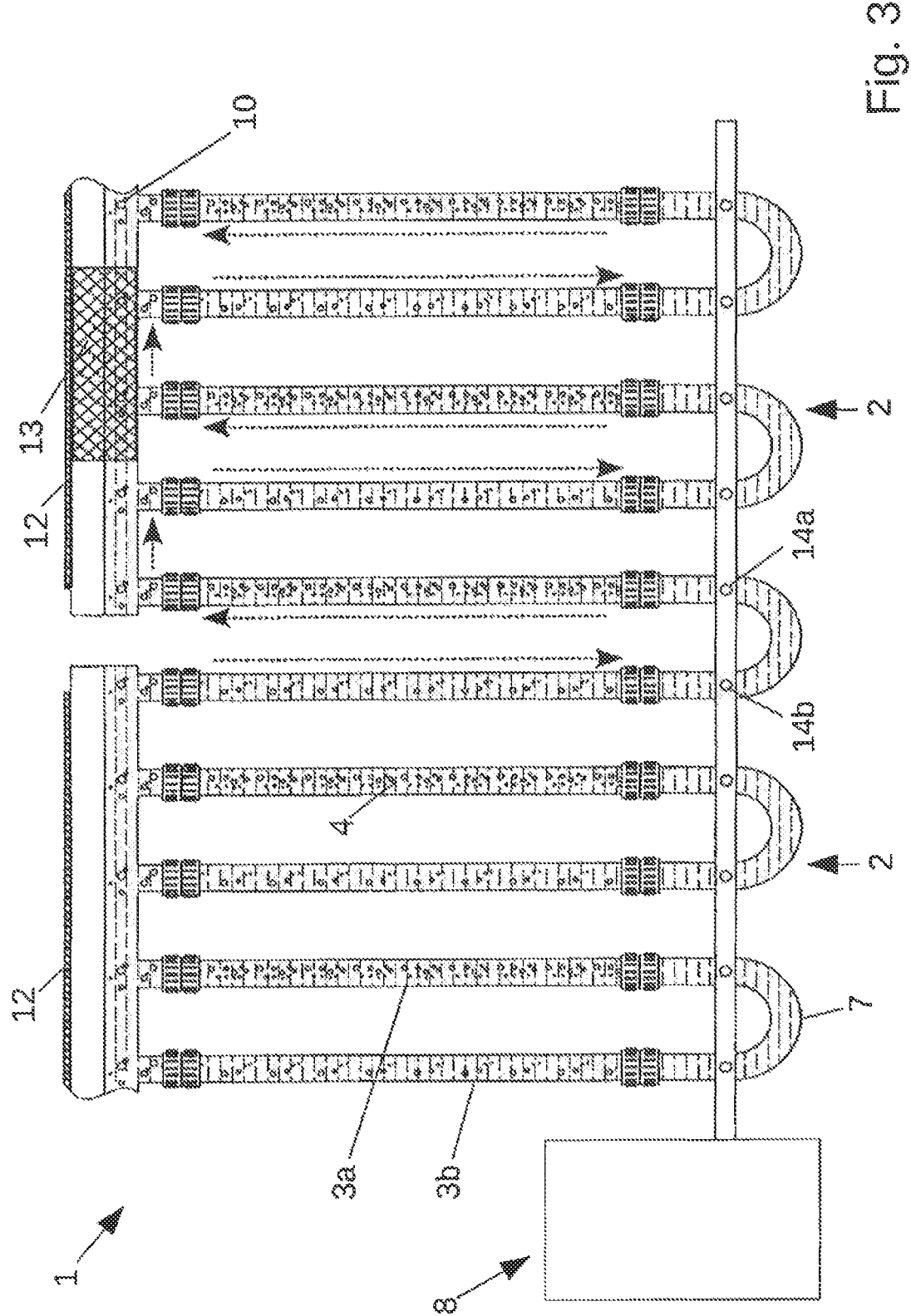

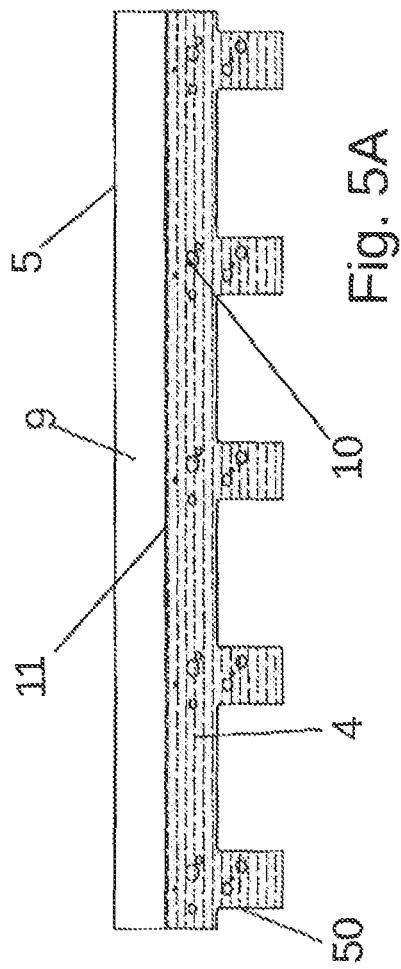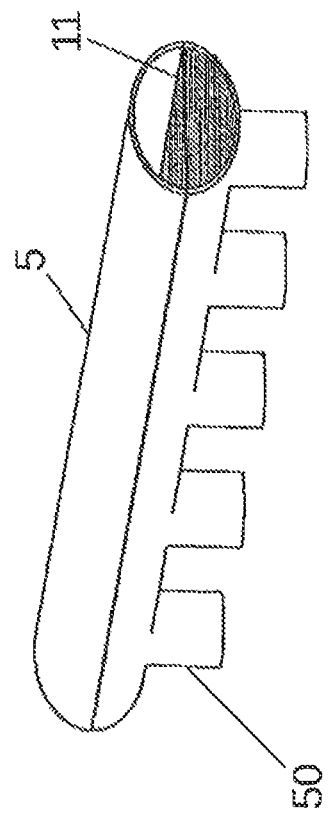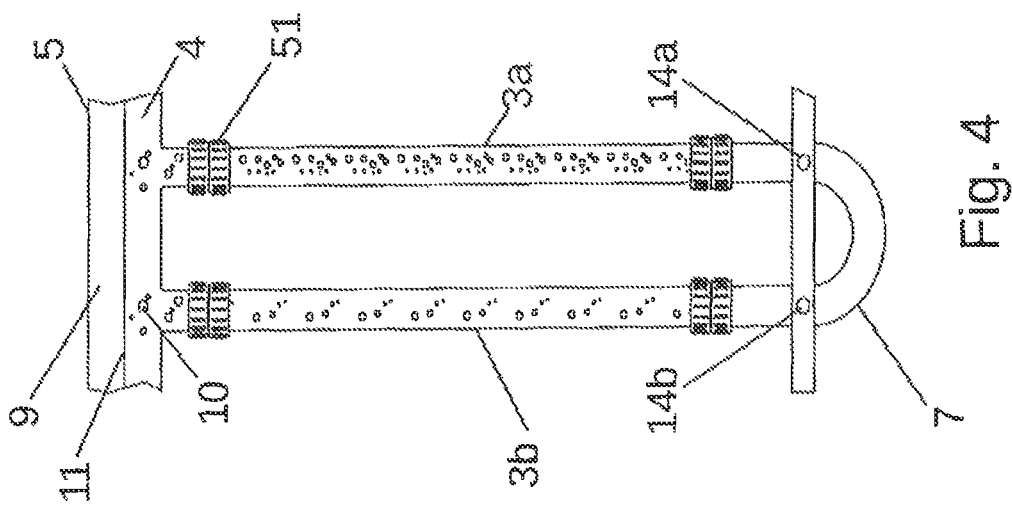

PHOTOBIOREACTOR AND METHOD FOR THE CULTIVATING OF MICROALGAE

The field of the present invention is that of photobioreactors for the cultivation of phototrophic microorganisms such as microalgae.

Phototrophic microorganisms such as microalgae are mainly cultivated because of their valuable ingredients, which are needed, for example, in the production of medical preparations, food and feed, dietary supplements, and cosmetics. These ingredients include, among others, unsaturated fatty acids (for example, omega-3 and omega-6 fatty acids), antioxidants such as astaxanthin and lutein, and chlorophyll. The composition of the ingredients depends on the cultivated nature of phototrophic microorganisms. A pure culture of phototrophic microorganisms is predominantly used to be able to ensure a certain quality or minimum concentration of the desired ingredients.

Usually, the microorganisms operating the photosynthesis are cultivated under the action of light (for example, sunlight) in the nutrient-containing culture medium in a photobioreactor, and then concentrated and processed. The ingredients can be extracted from the biomass obtained for further processing or the biomass itself can be used, for example, as feed or fertilizer.

One construction of photobioreactors for the cultivation of phototrophic microorganisms known in the prior art is that of the vertical tubular reactor in which upright, parallel, substantially transparent tubes (also sometimes referred to as columns) are connected in series and are in most cases flown through in meandering form by the culture medium having the phototrophic microorganisms. A photobioreactor of this construction is known, for example, from US 2014/0242681 A1.

In general, the tubes of a photobioreactor, in particular in continuous operation, are susceptible to contamination over time. Often in this case, residues from cultivation (for example, from remnants of dead microorganisms) accumulate on the inside of the tubes. This can, on the one hand, reduce the luminous efficacy (since these residues typically absorb light) and, on the other hand, represent a constant danger with regard to contamination of the culture medium with unwanted microorganisms, which find a suitable nutrient medium in the residues. In turn, the yield from the cultivation can be significantly reduced due to reduced luminous efficacy or contamination. Furthermore, it may be of great importance for product safety, in particular for sensitive domains such as the production of medical preparations or food supplements, to exclude as much as possible contamination of the culture with unwanted (and sometimes even toxic) microorganisms.

WO 2009/051478 A2 relates to photobioreactor having a cleaning system. Between stations, a cleaning too. (e.g., a cylindrical sponge, see also FIG. 2-5 of the document) can be pumped back and forth for cleaning the reactor tube inner walls (see page 12, 2nd paragraph). In the document, the tubes of the photobioreactor are disclosed as being connected via U-shaped connecting pieces (see FIG. 1, reference numeral 5, of the document) and not as gassed.

WO 2015/179888 A1 discloses a reactor of the vertical type. This reactor consists of at least one reactor element, which is formed of at least two upright connected tubes or chambers, wherein the individual reactor elements have inlet and outlet openings at the bottom at each of the outermost tubes or chambers, wherein the inlet opening in each case is associated with an ascending branch against the direction of gravity, and the outlet opening is associated with a descending branch in the direction of gravity, that all connections in the lower area, in particular the inlet opening, the outlet opening and the introduction inlet, are bathed with the reaction medium. From FIG. 1 or FIG. 3 of the document, it can be seen that the tubes or chambers in the reactor element "are connected in series" (see also page 14, line 19, of the document), that is, that never more than two tubes or chambers in the reactor element are disclosed as directly connected to each other. According to one embodiment, the reactor element is closed at the top with a closure element, wherein the closure element is designed to be removable in order to be able to clean the system (p. 16, 1st paragraph, of the document).

A further approach to the problem outlined above is supposed to have found the state of the art in the "one-way" photobioreactor. In this case, the reactor components such as tubes are made of comparatively inexpensive plastic material, which is replaced again after short operation.

Thus, US 2011/0027875 A1 relates to a low-cost, vertical photobioreactor for production use. According to the illustrated embodiments of the document, in this photobioreactor, substantially vertically oriented, parallel, transparent columns or tubes are connected to each other by lower and upper U-shaped connecting pieces, so that the cultural medium having microalgae can flow meandering through the photobioreactor in a closed circle during operation. The tubes or columns (or the culture medium therein) are gassed with carbon dioxide, which is known to be converted to oxygen by the microalgae. The lower and upper U-shaped connecting pieces can each be connected to a gas manifold (see FIG. 1, which depicts the lower portion of FIG. 1 of said document). A flexible low density polyethylene ("flexible LDP bag material") is proposed as a material for the columns or tubes. According to paragraphs [0087]-[0090], this material is discarded in the case of an unfavorable state of the microalgae culture, the U-shaped connecting pieces are separated from the gas manifold and, for example, cleaned in a dishwasher.

This approach to cleaning or keeping clean photobioreactors in the prior art is associated with many disadvantages, among others, causing (especially in large production facilities) high manual labor and long downtime, which diminish the yield of the photobioreactor with time. Furthermore, the high consumption of material (usually plastic) adversely affects the overall ecological balance of photobioreactor operation.

It is an object of the present invention to simplify the cleaning or keeping clean of a photobioreactor for the cultivation of phototrophic microorganisms. As a result, the service life or yield of the photobioreactor can be increased and the operating costs can be reduced.

The present invention provides a photobioreactor for cultivating phototrophic microorganisms, having a reactor element that comprises a plurality of risers and down pipes for liquid culture medium that contains the microorganisms and a manifold. The risers (in other words rising pipes) and down pipes are each connected in a liquid-permeable manner at their upper end to the manifold. At least one of the risers and one of the down pipes are additionally connected to each other in a liquid-permeable manner by a connecting piece. The photobioreactor also comprises a device for introducing gas into at least one riser. The photobioreactor according to the invention is designed such that both culture medium and, above the culture medium, a gas space for receiving gas bubbles rising from the culture medium, are present in the operating state in the manifold, wherein an interface is arranged between the culture medium and the gas space in the manifold. The stated object is achieved as a result.

Accordingly, the invention also provides a method of cultivating phototrophic microorganisms. This includes exposing a photobioreactor to light, wherein the photobioreactor is provided with a reactor element which comprises a plurality of risers and down pipes for liquid culture medium that contains the microorganisms, and a manifold, wherein the risers and down pipes are each connected in a liquid-permeable manner at their upper end to the manifold, wherein at least one of the risers and one of the down pipes are additionally connected in a liquid-permeable manner to each another by a connecting piece, and wherein the photobioreactor contains liquid culture medium having the microorganisms in the risers and down pipes, which culture medium is at least partially gassed. Both liquid culture medium having the microorganisms and a gas space above the culture medium are present in the manifold, wherein an interface is formed between the culture medium and the gas space in the manifold, and the gas space receives gas bubbles rising from the culture medium. This also solves the stated problem.

During the development of the present embodiment, it has been found that it is precisely the inner surfaces of a photobioreactor (or the "interface space" in the immediate vicinity of the interface) which are in contact with the interface between the culture medium and the gas space, which are susceptible to contamination, wherein generally more and more contamination accumulates with the duration of operation. In the region of the interface (which often varies slightly in height over the period of operation), foaming and deposition of dried residues of the phototrophic microorganisms can occur again and again. In particular, when a gassing of the photobioreactor is provided, the occurrence of such pollution-prone interfaces (or interface areas) in the photobioreactor can hardly be avoided. In addition, the gas bubbles rising from the culture medium cause the inner surface of the photobioreactor to be spattered with culture medium and these spatters also dry over time and thereby form contaminants. When said interfaces are located in more difficult-to-access regions, as shown in FIG. 1 (see in particular the uppermost curved arrows in FIG. 1), often nothing remains for cleaning except the temporary dismantling of the photobioreactor, such as disclosed in US 2011/0027875 A1.

The present invention is now based, among other things, on the finding that the cleaning or keeping clean of the photobioreactor is substantially facilitated by the fact that said interfaces of more difficult to access regions are shifted by the construction according to the invention or the operation of the photobioreactor according to the invention in a (more accessible) manifold and collected there to form an interface.

It has unexpectedly been found that in the photobioreactor according to the invention, a meandering flow can nevertheless be maintained, although in the prior art, U-shaped connecting pieces are usually provided both at the upper and at the lower end of the risers or down pipes to ensure the meandering flow, (see, for example, US 2014/0242681 A1 or US 2011/0027875 A1). Therefore, in a preferred embodiment of the method according to the invention, the culture medium flows through the risers and down pipes in meandering fashion. An advantage of the meandering flow is that the maturation of the phototrophic microorganisms is more controlled because microorganisms of similar maturity are separated from one another in the culture medium to a lesser extent than would be the case with chaotic flow (for example, when there are turbulences or different flow paths). Thus, microorganisms of similar maturity can also be more easily removed together from the photobioreactor.

It has proved to be particularly advantageous for the stabilization of the meandering flow when at least two reactor elements are provided in the photobioreactor, wherein a down pipe of the first reactor element and a riser of the second reactor element are connected to each another in a liquid-permeable manner by a connecting piece.

In a preferred embodiment, in the operating state a meandering flow of the culture medium through the risers and down pipes is achieved in that the culture medium is gassed more strongly in the riser connected to the down pipe by the connecting piece than in the down pipe. In this context, it is also possible to speak of a "gas lift" effect. An advantage of this design is that in operation on pumps (which are usually harmful to the phototrophic microorganisms by the shear forces they cause) can at least largely be dispensed with. A further advantage is that the inner surfaces of the risers or down pipes are kept cleaner by the frequent contact with rising gas bubbles.

Conveniently, therefore, in the operating state of the photobioreactor, agitation and/or flow of the culture medium is substantially caused by the gas bubbles rising in the culture medium.

In a particularly preferred embodiment, a device for guiding a maintenance device which is movable in the manifold is provided on the manifold. This can be, for example, a guide rail, a guide wire, or a bar with positioning marks which can be read by the maintenance device. In particular, when the device for guiding is magnetic, it can also be attached on the outside of the manifold. The maintenance device can free, that is, clean or keep clean, the inner surface of the manifold of any dried residues, in particular in the region of the interface, with the aid of spray nozzles, brushes and/or wiper blades.

In a preferred embodiment of the method according to the invention, the inner surface of the manifold is cleaned by the movable maintenance device, preferably at pre-settable time intervals. Advantageously, this happens during operation, so that losses in the yield are avoided as much as possible. It is expedient when the maintenance device can be flowed around within the manifold.

The construction according to the present invention allows for the ability to use (higher quality) glass components rather than disposable plastic components, among other things because the risk of glass breakage decreases when disassembly for cleaning is less often required. Thus, in a preferred embodiment of the photobioreactor, the risers and down pipes and/or the manifold substantially are made of glass. As a result, among other things, the longevity or resistance of the photobioreactor is increased, in particular when microalgae are cultivated, which require a culture medium having an extreme pH value. In addition, glass typically roughens less with time than commonly used plastic, so that cleaning or keeping clean is simplified. The glass can be coated, as disclosed, for example, in DE 10 2009 029 792 A1 or WO 2011/015653 A2.

According to a further preferred embodiment, an inlet for gassing with the device is provided for the riser connected to the down pipe by the connecting piece, and a further inlet for gassing with the device is provided for the down pipe connected to the riser by the connecting piece. As a result, different strengths of gassing of the risers and down pipes can be made possible. When gassing via the same gas line, this can be achieved, for example, by providing a gassing inlet of the riser with one or more openings (for example, in the form of membranes or sintered disks) that are altogether more permeable than that of the gassing inlet of the down pipe. Alternatively, the riser (that is, the gassing inlet of the riser) can be gassed e.g. via a first gas line having a pressure A, while the down pipe (that is, the gassing inlet of the down pipe) is gassed via a second gas line having a pressure B, wherein A is greater than B.

It is particularly advantageous when at least one of the inlets for gassing is provided in the connecting piece, because this is easier to accomplish in the construction of the photobioreactor. Namely, the connecting piece can be made (continuously) of easily machinable, non-transparent materials such as stainless steel.

The photobioreactor of the present invention is preferably a type of tubular reactor, more specifically, a vertical tubular reactor, or not a plate reactor or flat panel reactor.

According to the invention, said plurality of risers or down pipes of the reactor element, which are connected in a liquid-permeable manner to the same manifold, is at least three (for example, in the arrangement down pipe-riser-down pipe or riser-down pipe-riser along the manifold). It is favorable in terms of scalability of the cleaning, when said plurality is at least four, preferably at least five, more preferably at least ten, even more preferably at least twenty, in particular at least thirty or even at least forty. Advantageously, an alternating arrangement of risers or down pipes is selected along the manifold (that is, for example, riser-down pipe-riser- . . . -down pipe-riser or riser-down pipe-riser- . . . -down pipe-riser-down pipe, or down pipe-riser-down pipe- . . . -riser). Expediently, the positioning of inlets or outlets (for example, at the top or bottom end) in the photobioreactor according to this arrangement is to naturally be chosen so that a dead volume is avoided. It is evident to a person skilled in the art that by reversing the flow of the culture medium (for example, by changing the gassing), a riser can become a down pipe or vice versa. Advantageously, a flow velocity vector results from the sum of the flow velocity vectors of the flows of the culture medium prevailing in the manifold (in particular when a meandering flow is conducted in the reactor element), which flow velocity vector is substantially parallel to the longitudinal axis of the manifold (a net flow along the longitudinal axis, so to speak, see also the horizontal dashed arrows in FIG. 3).

It is favorable when the longitudinal axes of the riser or down pipes, optionally independently of each another, are at an angle of more than 5°, preferably more than 20°, more preferably more than 40° or even more than 60° more preferably more than 70° or even more than 80°, in particular more than 85° or even more than 87.5° to the level of the culture medium or to the manifold. It is particularly favorable when the longitudinal axes of the riser or down pipes are substantially normal (or normal) to the level of the culture medium or to the (preferably substantially horizontal) manifold (in other words, when they are oriented vertically). Expediently, the longitudinal axes of the risers and down pipes (in particular of those which are each connected by a connecting piece) are substantially parallel to each other.

The manifold comprises, according to the definition of the invention, at least three liquid-permeable connections for risers and down pipes. These can, for example, be formed as bores, openings or connection extensions (said interface must, however, be located inside the manifold itself (in other words: in the main tube of the manifold) in order to ensure simplified cleaning). It is favorable when the manifold, along its longitudinal axis, does not comprise a slope or rise at an angle (with respect to the level of the culture medium) of greater than 10°, preferably of greater than 5°, more preferably greater than 2.5°, even more preferably greater than 1° or even greater than 0.5°. Particularly preferably, the manifold (along its longitudinal axis) is oriented substantially horizontally or horizontally (that is, its longitudinal axis is substantially parallel or parallel to the level of the culture medium).

In the context of the invention, the gas space in the manifold (which is located above the culture medium in the manifold) is preferably a gas space which extends along the longitudinal axis of the manifold over at least 10%, preferably at least 20% or even at least 30%, more preferably at least 40% or even at least 50%, even more preferably at least 60% or even at least 70%, in particular at least 80% or even at least 90% of the length of the manifold. It is particularly expedient when said gas space extends over the entire length of the manifold. It is understood that "gas" can also be understood as a gas mixture.

To facilitate cleaning, the manifold and/or the risers or down pipes, expediently, optionally independently of each other, along their longitudinal axis, comprise no bending of more than 90°, preferably more than 70°, more preferably more than 50°, even more preferably more than 30 or even more than 20°, in particular of more than 10° or even more than 5°. It is particularly favorable when the manifold and/or the risers or down pipes are substantially straight or straight along their longitudinal axis. Preferably, the manifold and/or the risers or down pipes (if necessary, except for any connection extensions) have a substantially round profile.

For the entire context of the invention, a connecting piece preferably connects exactly one of the risers with exactly one of the down pipes in a liquid-permeable manner (or the two adjoin one another in a liquid-permeable manner). It is preferred in this case that at least all except one or two risers of the reactor element and/or at least all except one or two down pipes of the reactor element are each pairwise connected in a liquid-permeable manner with such a connecting piece, in particular at least all except one riser of the reactor element and/or at least all except one down pipe of the reactor element are each pairwise connected to such a connecting piece in a liquid-permeable manner. It is structurally favorable (in particular to support a meandering flow) when a connecting piece connects a riser and a down pipe that are adjacent to each other (that is, are adjacently connected to the manifold) to each other in a liquid-permeable manner.

"Operating state" herein is understood to mean a state of the photobioreactor in which live phototrophic microorganisms are cultivated in culture medium in the photobioreactor, wherein the culture medium in the photobioreactor preferably comprises a flow (in particular substantially caused by the gassing).

The present invention further relates to the following aspects or embodiments:

Embodiment 1. A photobioreactor for cultivating phototrophic microorganisms, having a reactor element that comprises a tube, and having a maintenance device and a drive system that can move the maintenance device in the tube, wherein the photobioreactor is designed such that in the operating state of the photobioreactor, liquid culture medium having microorganisms at least partially flows through the tube, characterized in that the photobioreactor is designed such that the maintenance device can be used in the tube in the operating state of the photobioreactor and can be moved by the drive system at least against the flow of the culture medium in the tube.

Embodiment 2. The photobioreactor according to embodiment 1, characterized in that the photobioreactor further comprises a device for gassing the culture medium, wherein the photobioreactor is designed such that in the operating state of the photobioreactor, the maintenance device in the tube is brought into contact with gas bubbles located in the culture medium.

Embodiment 3. The photobioreactor according to embodiment 1 or 2, characterized in that in the operating state of the photobioreactor, the culture medium can flow around and/or flow through the maintenance device in the tube.

Embodiment 4. The photobioreactor according to one of the embodiments 1 to 3, characterized in that the photobioreactor is designed such that both culture medium and, above the culture medium, a gas space for receiving gas bubbles rising from the culture medium, are present in the operating state in the tube, wherein in the tube, an interface is arranged between the culture medium and the gas space, and the maintenance device is set up at least for cleaning inner surface of the tube which inner surface is in contact with the gas space.

Embodiment 5. The photobioreactor according to one of embodiments 1 to 4, characterized in that the maintenance device comprises a spray nozzle for spraying the inner surface of the tube with a cleaning liquid, preferably wherein the maintenance device is set up at least for spraying inner surface of the tube through the spray nozzle which inner surface is in contact with said gas space.

Embodiment 6. The photobioreactor according to one of the embodiments 1 to 5, characterized in that the maintenance device comprises at least one wiper blade made of an elastic material for wiping the inner surface of the tube, preferably wherein the maintenance device is set up at least for wiping inner surface of the tube with the wiper blade which inner surface is in contact with said gas space and/or preferably wherein the maintenance device comprises an optionally further, spray nozzle, which is set up for spraying the wiper blade with a cleaning liquid.

Embodiment 7. The photobioreactor according to embodiment 5 or 6, wherein the spray nozzle is connected via a line to a liquid reservoir outside the tube.

Embodiment 8. The photobioreactor according to one of the embodiments 1 to 8, characterized in that the tube is a manifold having at least three connections for the inflow or outflow of culture medium, and the photobioreactor is designed such that the maintenance device can be moved to at least one of the connections in the tube and can seal the connection.

Embodiment 9. The photobioreactor according to embodiment 8, characterized in that the reactor element further comprises a plurality of risers and down pipes for the liquid culture medium, wherein the risers and down pipes are each connected in a liquid-permeable manner at their upper end to the tube formed as a manifold, wherein at least one of the risers and one of the down pipes are additionally connected in a liquid-permeable manner to each other by a connecting piece, and wherein the photobioreactor is designed such that the maintenance device at the same time can seal the down pipe connection and the riser connection, both of which are additionally connected to each other in a liquid-permeable manner by a connecting piece.

Embodiment 10. The photobioreactor according to embodiment 9, characterized in that the maintenance device is set up to clean the down tube sealed by the maintenance device relative to the tube and the riser sealed by the maintenance device relative to the tube, both of which are connected to each other in a liquid-permeable manner by a connecting piece.

Embodiment 11. The photobioreactor according to one of the embodiments 1 to 10, characterized in that on the tube, preferably on the outside, is provided a guide bar for stabilizing and/or positioning the maintenance device in the tube.

Embodiment 12. The photobioreactor according to one of the embodiments 1 to 11, characterized in that the drive system comprises at least one cable winch, which can drive a cable guided in the tube and connected to the maintenance device, preferably wherein the cable winch is equipped with a device for disinfecting the cable.

Embodiment 13. The photobioreactor according to one of the embodiments 1 to 12, characterized in that the maintenance device comprises at least two modules which are connected to each other by a coupling, preferably wherein the tube is made substantially of glass.

Embodiment 14. The photobioreactor according to one of the embodiments 1 to 13, characterized in that the photobioreactor comprises a station for the maintenance device, which is set up for cleaning the maintenance device and in which the maintenance device can be moved.

Embodiment 15. A method of cultivating phototrophic microorganisms in a photobioreactor, wherein the photobioreactor is equipped with a reactor element that comprises a tube and with a maintenance device in the tube and with a drive system that moves the maintenance device in the tube, wherein liquid culture medium having the microorganisms at least partially flows through the tube, characterized in that the method comprises the use of the maintenance device in the tube in the operating state of the photobioreactor and the maintenance device is moved by the drive system at least against the flow of the culture medium in the tube, preferably wherein the photobioreactor is further defined according to one of embodiments 1 to 11.

Embodiment 16. A movable maintenance device for the maintenance of the inner surface of a tube of a photobioreactor for the cultivation of phototrophic microorganisms, characterized in that the maintenance device is suitable for the maintenance of the inner surface of the tube in ongoing operation of the photobioreactor, while liquid culture medium having the microorganisms at least partially flows through the tube, and that the maintenance device is set up co be moved by an external drive system, which preferably comprises a cable winch, at least against the flow of the culture medium in the tube.

Embodiment 17. The movable maintenance device according to Embodiment 16, characterized in that the maintenance device comprises a spray nozzle for spraying the inner surface of the tube with a cleaning liquid and a connection for a line with the liquid.

Embodiment 18. The movable maintenance device according to embodiment 16 or 17, characterized in that the maintenance device comprises at least one wiper blade made of an elastic material for wiping the inner surface of the tube, preferably wherein the maintenance device comprises a, possibly further, spray nozzle which is set up for spraying the wiper blade with a cleaning liquid.

Embodiment 19. The movable maintenance device according to one of the embodiments 16 to 18, characterized in that the maintenance device comprises at least two modules which are connected to each other by a coupling.

Embodiment 20. The movable maintenance device according to one of the embodiments 16 to 19, characterized in that the maintenance device is further equipped with a device for sealing of connections of the tube.

Embodiment 21. A use of the movable maintenance device according to one of the embodiments 16 to 20 for maintaining the inner surface of a tube of a photobioreactor for cultivating phototrophic microorganisms, wherein maintenance takes place during ongoing operation of the photobioreactor, wherein liquid culture medium having the microorganisms at least partially flows through the tube.

The invention is further elucidated on the basis of particularly preferred embodiments, to which, however, it is not limited, and with reference to drawings. The drawings show in detail:

FIG. 3 shows a plan view of an embodiment of the photobioreactor according to the invention having a maintenance device in the operating state;

FIG. 4 is a locally enlarged view of the embodiments of FIG. 2 or FIG. 3;

FIG. 5A shows a plan view of a filled manifold as can be used for the present invention;

FIG. 5B shows a perspective view of the manifold according to FIG. 5A;

Figure 1:
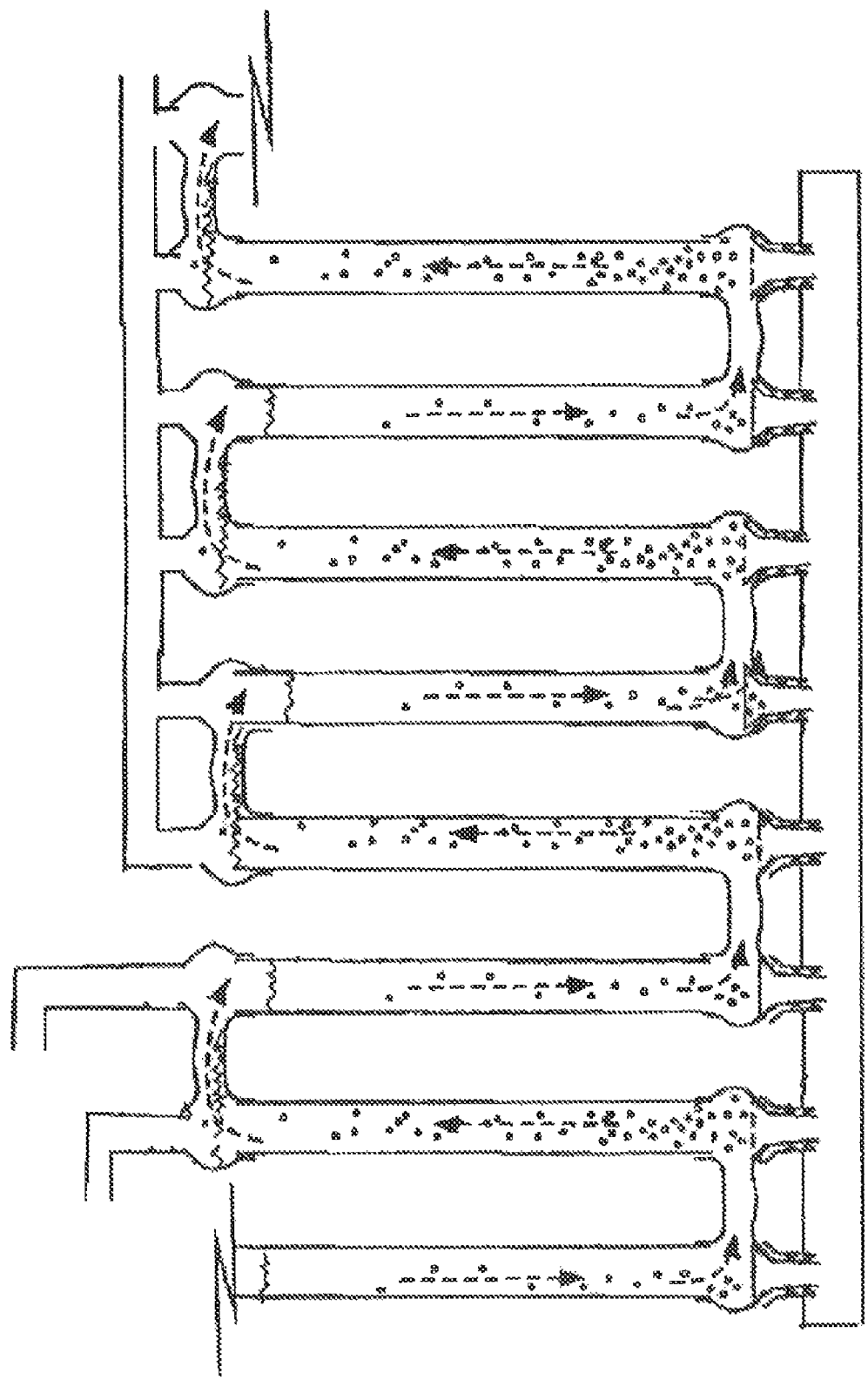
FIG. 1 shows a photobioreactor according to the prior art (US 2011/0027875 A1), in which the interfaces between culture medium and gas space are located below the upper gas manifold.
Figure 2:
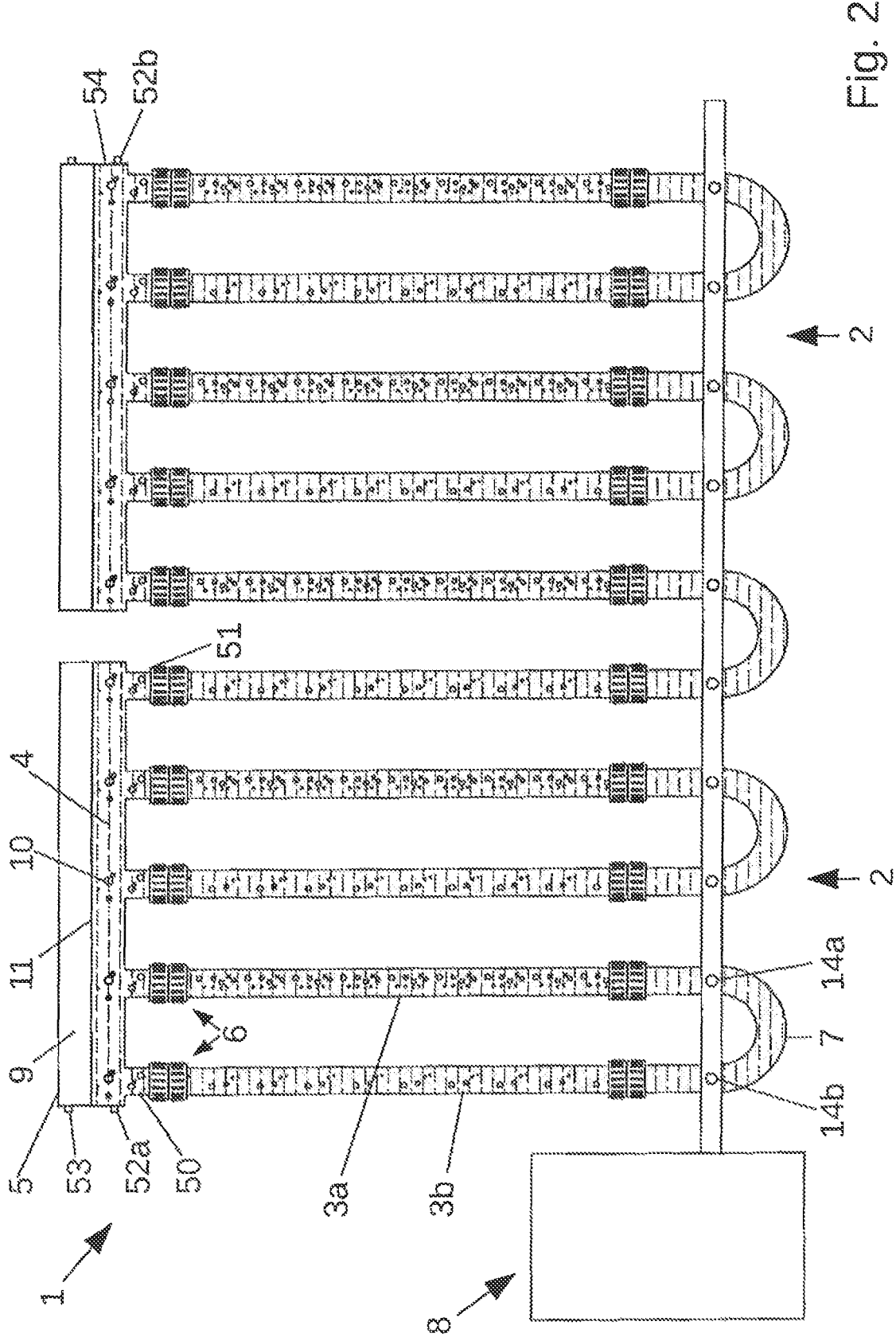
FIG. 2 shows a plan view of an embodiment of the photobioreactor according to the invention in the operating state.

FIG. 2 shows a photobioreactor 1 for cultivating phototrophic microorganisms, having two reactor elements 2 that each comprise a plurality of vertical straight risers 3a and down pipes 3b for culture medium 4 and a horizontal, straight manifold 5. The culture medium 4 is a liquid culture medium based on water and enriched with nutrients; it contains the phototrophic microorganisms (usually microalgae). Said tubes are made of glass, wherein the manifolds 5 are provided with connection extensions 50 (see also FIG. 5A and FIG. 5B). The risers 3a and down pipes 3b are each connected in a liquid-permeable manner at their upper end 6 with the aid of the tube connectors 51 to the connection extensions 50 of the manifold 5. The risers 3a and the down pipes 3b are additionally connected to each other in a liquid-permeable manner by a respective U-shaped connecting piece 7 (see also FIG. 4).

The photobioreactor 1 further comprises a device 8 for introducing carbon dioxide (and/or compressed air) into the risers 3a or the down pipes 3b. An inlet 14a for gassing by the device 8 is provided for the riser 3a connected to the down pipe 3b through the connecting piece 7. A further inlet 14b is provided for gassing by the device 8 for the down pipe 3b connected to the riser 3a through the connecting piece 7. The carbon dioxide is pumped from a liquid tank into a gas manifold by a gas pump. The connections of the gas manifold are connected to one inlet 14a and 14b, respectively by hoses. By providing an opening of the inlet 14a, which is more permeable than the opening of the inlet 14b, a greater gassing of the risers 3a relative to the down pipes 3b is made possible. As a result, surprisingly, although no U-shaped connecting pieces 7 are provided at the respective upper end 6 of the risers 3a or down pipes 3b, but the manifold 5 is provided, a meandering flow of the culture medium 4 is created (upwards in the risers 3a, downward into the down pipes 3b, see also the dashed arrows in FIG. 3). This meandering flow is additionally stabilized further in that the two reactor elements 2 are connected to each other in a liquid-permeable manner through a U-shaped connecting piece 7 via a down pipe 3b of the first reactor element 2 to a riser 3a of the second reactor element 2, that is, in simplified terms, by providing a "gap" between the two manifolds 5.

The inlet 52a and the outlet 52b can be connected to each other by a hose, thereby allowing cyclical operation of the photobioreactor 1. After a certain number of cycles under exposure with light, the culture medium 4, which now contains a significantly higher concentration of microorganisms, can be removed at the outlet 52b for harvesting (that is, for concentration and drying of the phototrophic microorganisms), while fresh culture medium 4 having a low initial concentration of phototrophic microorganisms is introduced at the inlet 52a. Of course, a continuous cyclic operation is also conceivable in which the inlet 52a remains connected to the outlet 52b by a hose, and fresh culture medium 5 is continuously supplied at an inlet in a first lower connecting piece 7 and the same amount of denser culture medium 4 is continuously removed at an outlet in a second lower connecting piece 7 which lies directly in front of the connecting piece 7 seen in the flow direction. This naturally requires a certain minimum length of the breeding line. Also, when the photobioreactor 1 has a certain minimum length, a continuous linear operation is also conceivable in which fresh culture medium 4 having a low initial concentration of phototrophic microorganisms is continuously introduced at the inlet 52a and the same amount of mature culture medium 4 is continuously removed at the outlet 52b for harvesting. Inlets, however, can also be provided at other locations of the reactor (for example, U-bend connecting piece of the first/last riser or down pipe, but also in another U-bend connecting piece in the photobioreactor).

The meandering flowing culture medium 4 having the phototrophic microorganisms is so high in the reactor elements 2 that also the manifolds 5 are each filled about halfway therewith. Thus, both culture medium 4 and, above the culture medium 4, a gas space 9 for receiving gas bubbles 10 rising from the culture medium 4 are present in the manifold 5, wherein an interface 11 is arranged between the culture medium 4 and the gas space 9 in the manifold 5. The gas pressure equalization with the environment takes place via the valve 53 which is equipped with a filter system in order to avoid contamination of the culture medium 4.

The contamination associated with the interface 11 between culture medium 4 and gas space 9 on the inner surface of the manifold 5 can be cleaned with relatively little effort in that the photobioreactor 1 is briefly taken out of service, the culture medium 4 is discharged from the manifold 5, the cover plate 54 of the manifold is removed and the inner surface of the manifold is cleaned, for example, with a brush attached to a telescopic pole.

The embodiment of the photobioreactor 1 shown in FIG. 3 enables the cleaning or keeping clean of the inner surface of the manifold 5 during operation. In this case, the guide bar 12 is provided on the manifold 5 for the movable maintenance device 13. The maintenance device 13 is equipped with brushes and spray nozzles for the inner surface of the manifold 5. The maintenance device 13 is, for example, magnetic and can be moved by a magnet (or cables) displaceable in the guide bar 12. The maintenance device 13 can be flowed around and can be used at pre-settable time intervals during ongoing operation, which substantially reduces the idle times of the photobioreactor 1. The dashed arrows illustrate the flow path in the reactor element 2.

Figure 6:
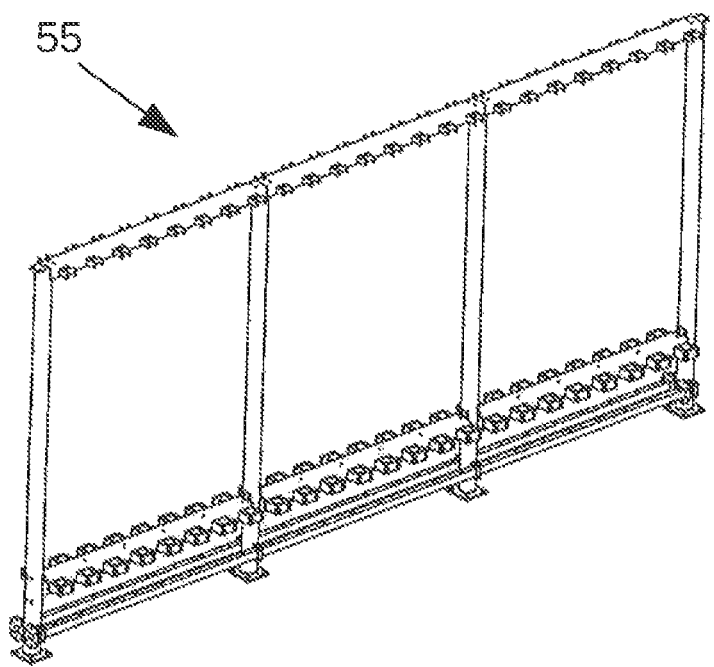
FIG. 6 shows a perspective view of a metal framework, as can be for embodiments of reactor elements of the photobioreactor according to the invention.
Figure 7:
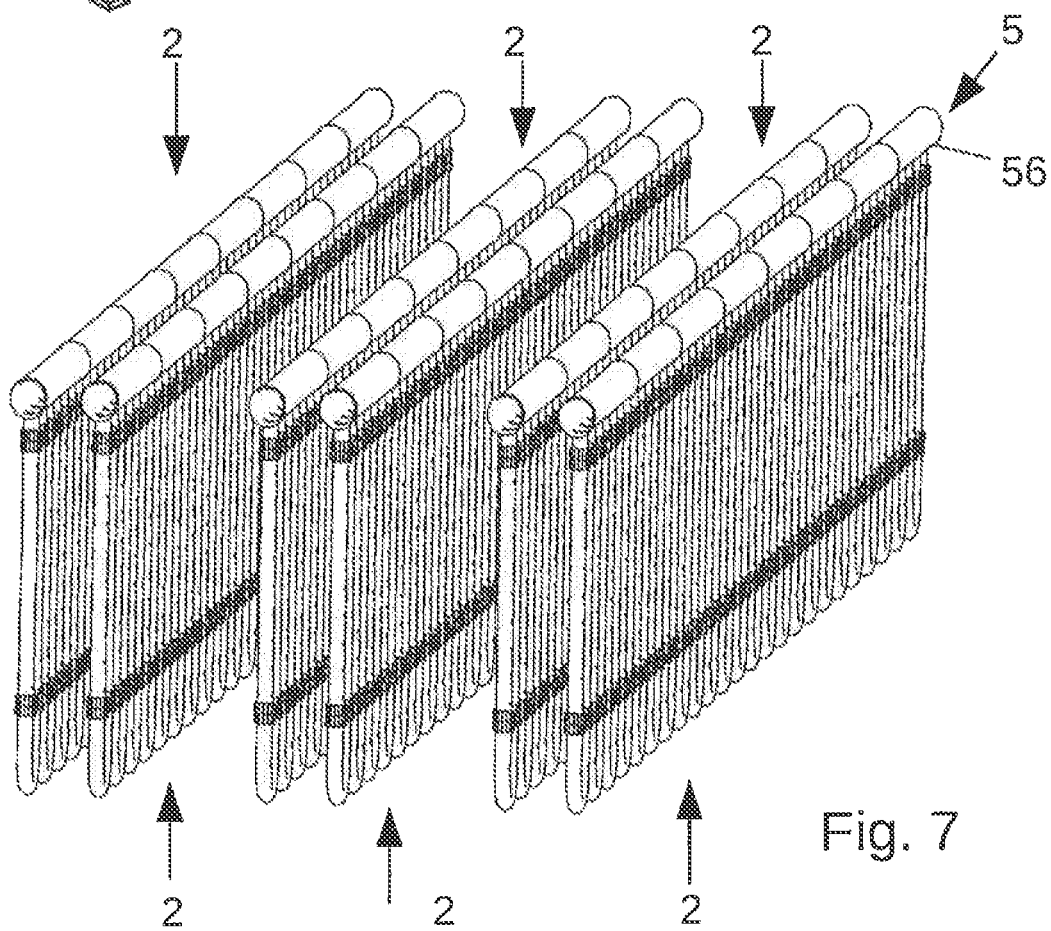
FIG. 7 shows a perspective view of reactor elements of one embodiment of the photobioreactor according to the invention.

FIG. 7 schematically shows an embodiment of the photobioreactor 1 in which the respective manifold 5 of a reactor element 2 is made of glass parts 56 which are directly connected to each other. In each case, two reactor elements 2 are held by the metal frame 55 shown in FIG. 6.

The invention claimed is:

1. A photobioreactor for the cultivation of phototropic organisms, comprising
    at least one a reactor element that comprises;
    a plurality of vertical risers and down pipes for a liquid culture medium containing the phototrophic microorganisms;
    a manifold oriented horizontally and configured so that each of the plurality of vertical risers and down pipes is connected in a liquid-permeable manner at an upper end of each of the plurality of vertical risers and down pipes to the manifold;
    at least one connecting piece configured to connect a lower end of one of the vertical risers to a lower end of one of the down pipes in a liquid-permeable manner;
    a gassing device for introducing gas into a riser of the plurality of vertical risers and down pipes,
    wherein, in an operating state of the photobioreactor in the manifold, the manifold is configured to contain the liquid culture medium and a gas space above the liquid culture medium for receiving gas bubbles rising from the liquid culture medium such that an interface is formed between the liquid culture medium and gas space whereby a pollution-prone interface zone is formed within the manifold where the interface contacts the manifold;
    a maintenance device configured to remain contained in the manifold and restricted to move within the manifold along its longitudinal axis, the maintenance device being configured to clean within the manifold at the interface where the pollution-prone interface zone is formed;
    wherein the maintenance device is sized to fit in an interior space of the manifold: wherein each of the vertical risers and the down pipes have an interior space smaller than the interior space of the manifold; and
    wherein the manifold further comprises a guiding device provided on the manifold and configured to horizontally guide the maintenance device and restrict movement of the maintenance device within the manifold along its longitudinal axis.

2. The photobioreactor according to claim 1, wherein the at least one reactor element comprises at least a first and a second reactor element, and
    wherein a lower end of a down pipe of the first reactor element and a lower end of a vertical riser of the second reactor element are connected to each other in a liquid-permeable manner by a further connecting piece.

3. The photobioreactor according to claim 1, wherein at least one of the plurality of vertical risers and down pipes or the manifold are made of glass.

4. The photobioreactor according to claim 1, wherein the one vertical riser of the plurality of vertical risers connected to the one down pipe comprises an inlet for gassing with the gassing device, and said one down pipe comprises a further inlet for gassing with the gassing device.

5. The photobioreactor according to claim 4, wherein at least one of the inlet and the further inlet for gassing is arranged in the connecting piece.

6. The photobioreactor according to claim 4, wherein in an operating state of the photobioreactor, at least one of agitation or flow of the liquid culture medium is caused by the gas bubbles rising in the liquid culture medium.

7. The photobioreactor according to claim 6, wherein, in an operating state of the photobioreactor, the liquid culture medium meanderingly flows through the plurality of vertical risers and down pipes, and
    wherein the liquid culture medium in the one vertical riser of the plurality of vertical risers connected to the one down pipe is gassed stronger than in said one down pipe.

8. A method for cultivating phototrophic microorganisms in a photobioreactor that includes: at least one reactor element having a plurality of vertical risers and down pipes for a liquid culture medium containing the microorganisms, a manifold oriented horizontally and configured so that each of the plurality of vertical risers and down pipes is connected in a liquid-permeable manner at its upper end to the manifold, and a maintenance device configured to remain contained in the manifold and to be movable within the manifold, wherein the maintenance device is sized to fit in an interior space of the manifold; wherein each of the vertical risers and the down pipes have an interior space smaller than the interior space of the manifold; wherein at least: a lower end of one of the vertical risers and a lower end of one of the down pipes are connected to each other in a liquid-permeable manner by a connecting piece, the method comprising:
    exposing the photobioreactor to light;
    at least partially gassing the liquid culture medium in the in at least one of the vertical risers or down pipes of the plurality of pipes and down pipes of the photobioreactor,
    wherein an interface is formed between the liquid culture medium in the manifold and a gas space in the manifold that receives gas bubbles rising from the liquid culture medium.

9. A method for cultivating phototrophic organisms in the photobioreactor according to claim 1, the method comprising:
    exposing the photobioreactor to light.

10. The method according to claim 8, further comprising flowing the liquid culture medium to meander through the plurality of vertical risers and down pipes.

11. The method according to claim 8, further comprising cleaning an inner surface of the manifold with the movable maintenance device.

12. The method according to claim 11, wherein the inner surface of the manifold is cleaned at pre-settable time intervals.

* * * * *